United States Patent

Philippe et al.

Patent Number: 5,091,522
Date of Patent: Feb. 25, 1992

[54] RETINOIC ESTERS OF D-DESOSAMINE, PROCESS FOR THEIR PREPARATION AND THEIR USE IN HUMAN OR VETERINARY MEDICINE AND IN COSMETIC COMPOSITIONS

[75] Inventors: Michel Philippe, Antony; Henri Sebag, Paris, both of France

[73] Assignee: L'Oreal, Paris, France

[21] Appl. No.: 493,117

[22] Filed: Mar. 15, 1990

[30] Foreign Application Priority Data

Mar. 16, 1989 [FR] France .................. 89 03460

[51] Int. Cl.$^5$ .................. A61K 31/70; A61K 7/48
[52] U.S. Cl. .................. 536/17.2; 536/7.1; 536/7.2; 536/16.2; 514/859; 514/844; 514/912; 514/825
[58] Field of Search .................. 536/4.1, 16.2, 7.4, 536/7.2, 7.1, 17.2, 18.7; 514/30, 29, 24, 529, 912, 560, 844, 859, 825, 25

[56] References Cited

U.S. PATENT DOCUMENTS

| | | | |
|---|---|---|---|
| 3,290,284 | 12/1966 | Newman | 536/17.2 |
| 3,669,952 | 6/1972 | Mallams | 536/7.1 |
| 3,669,953 | 6/1972 | Mallams | 536/7.1 |
| 4,921,839 | 5/1990 | Brain et al. | 514/29 |
| 4,957,905 | 9/1990 | Hunt | 514/29 |
| 4,994,491 | 2/1991 | Purcell et al. | 514/549 |
| 5,004,732 | 4/1991 | Philippe et al. | 514/29 |
| 5,004,733 | 4/1991 | Philippe et al. | 514/29 |

FOREIGN PATENT DOCUMENTS 253393 1/1988 European Pat. Off. .
2556348 6/1985 France .
2598420 11/1987 France .

Primary Examiner—Ronald W. Griffin
Assistant Examiner—Louise Leary
Attorney, Agent, or Firm—Cushman, Darby & Cushman

[57] ABSTRACT

Retinoic esters of D-desosamine have the formula

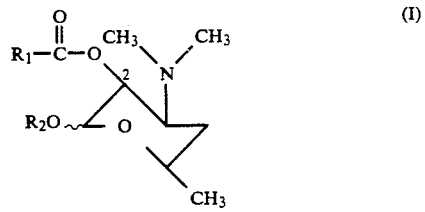

wherein the

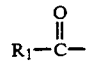

radical is (all trans) retinoyl, (13 cis) retinoyl or etretinoyl, and $R_2$ represents linear or branched alkyl having 1-24 carbon atoms; and the $\alpha$ and $\beta$ anomers, their mixtures and their salts.

These esters are usefully employed in human and veterinary medicines and in cosmetic compositions.

15 Claims, No Drawings

RETINOIC ESTERS OF D-DESOSAMINE, PROCESS FOR THEIR PREPARATION AND THEIR USE IN HUMAN OR VETERINARY MEDICINE AND IN COSMETIC COMPOSITIONS

The present invention relates to new retinoic esters of D-desosamine, to a process for their preparation and to their use in human and veterinary medicine and in cosmetic compositions.

These new retinoic esters of D-desosamine are particularly useful in pharmaceutical and cosmetic compositions intended, principally, to combat bacteria proliferation be it of infections origin or not.

The retinoic esters of D-desosamine of the present invention are also usefully employed in the topical and systemic treatment of dermatologic diseases linked to a keratinization disorder (differentiation-proliferation) and dermatologic diseases, or others, having inflammatory and/or immunoallergic components and in conjunctive tissue degeneration illnesses. These retinoic esters also exhibit anti-tumoral activity. Moreover, these esters can be employed in the treatment of atophy, be it cutaneous or respiratory and in the treatment of rheumatoid psoriasis.

The esters of the present invention can also be employed in treatments to combat skin aging.

They are also employed in the ophthalmologic field and principally in the treatment of corneopathies.

There have already been proposed, in French patent No. 84.18617 (2.556.348), new retinoids which are esters or amides of etretinic acid and a sugar, for the treatment of neoplasies, psoriasis and acne. These esters or amides have the formula

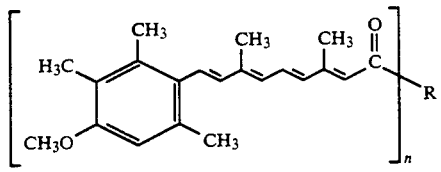

wherein

R represents the residue of a sugar linked by a bond of the ester type or the residue of an aminated sugar linked by an amide type bond, or derivatives of such sugars, and n is equal to 1 or 2.

In accordance with this French patent, the sugar residue is derived preferably from glucose, maltose, trehalose or ribose or even a derivative of these sugars.

After significant studies it has now been noted, in a quite surprising and unexpected manner, that by using, as the sugar, D-desosamine, forming various macrolids including erythromycins, for the formation of esters not only with etretinic acid but also with (all trans) and (13 cis) retinoic acids, it was possible to overcome the disadvantages of these acids, i.e. their toxicity and principally their teratogen characteristic.

The comparative studies carried out have, moreover, evidenced that these new properties were due essentially to the nature of the sugar employed for the esterification, namely, D-desosamine. In effect the esters corresponding to glucose, for example, do not provide the same detoxification and principally in that which concerns an all-trans chain.

Moreover, it has been established that these new retinoic esters of D-desosamine exhibit, in an unexpected manner, excellent anti-bacteria properties although the same esters of other carbon hydrates, such as glucose, have been established to be devoid of any such activity.

The present invention relates to, as a new industrial product, retinoic esters of D-desosamine having the following general formula

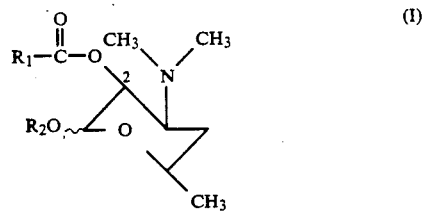

wherein

is either the (all trans) or (13 cis) retinoyl radical or the etretinoyl radical, and $R_2$ represents linear or branched alkyl having 1 to 24 carbon atoms, and the $\alpha$ and $\beta$ anomers and their mixture as well as the salts of the compounds of formula (I).

Representative linear or branched alkyl radicals having 1-24 carbon atoms, include principally, methyl, ethyl, propyl, isopropyl, butyl, tert. butyl, octyl, nonyl, decyl, undecyl, dodecyl, tetradecyl, hexadecyl, octadecyl and 2-decyl tetradecyl radicals.

When the retinoic esters of D-desosamine are derived from etretinic acid they can be represented by a compound of the following general formula

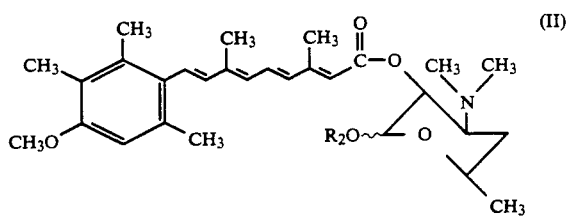

wherein $R_2$ has the same meaning given above in the definition of the compound of formula (I).

When the retinoic esters of D-desosamine are derived from all trans) or (13 cis) retinoic acid, they can be represented by the following general formula

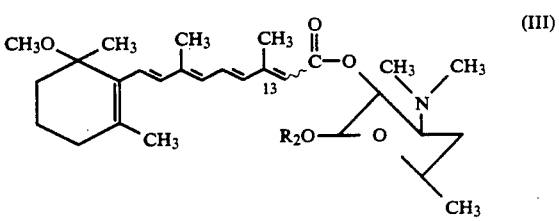

wherein $R_2$ has the same meaning as that given above in general formula (I).

Representative retinoic esters of D-desosamine in accordance with the present invention include, principally:

1. O-retinoyl (13 cis)-2-O-butyl-1-α,β-D-desosamine,
2. O-retinoyl (all trans)-2-O-butyl-1-α-β-D-desosamine,
3. O-retinoyl (all trans)-2-O-butyl-1-α-D-desosamine,
4. O-retinoyl (13 cis)-2-O-butyl-1-α-D-desosamine,
5. O-etretinoyl (all trans)-2-O-butyl-1-α,β-D-desosamine,
6. O-etretinoyl (all trans)-2-O-butyl-1-α-D-desosamine,
7. O-etretinoyl (all trans)-2-O-butyl-1-β-D-desosamine,
8. O-retinoyl (13 cis)-2-O-methyl-1-α,β-D-desosamine,
9. O-retinoyl (all trans)-2-O-decyl-2'-tetradecyl-1-α,β-D-desosamine, and
10. O-retinoyl (13 cis)-2-O-decyl-2'-tetradecyl-1-α,β-D-desosamine.

The present invention also relates to a process for preparing the retinoic esters of D-desosamine such as defined above.

Various processes for the esterification of D-desosamine in the 2-position can be employed, but, preferably the esterification is carried out in an anhydrous organic solvent medium such as tetrahydrofuran, alone or in admixture with another organic solvent such as pyridine or N,N-dimethylformamide, by reacting an excess of the mixed anhydride, of either etretinic acid or (all trans) retinoic or (13 cis) retinoic acid, prepared in situ, for example, from ethyl chloroformate and the selected acid, on a monoether, in position 1, of D-desosamine.

Other esterification procedures can be employed, and principally the method using the imidazolides of the selected acids in an anhydrous solvent, such as pyridine or N,N-dimethyl formamide in the presence of a base such as potassium tert. butanolate or sodium imidazolide. However, these methods generally give lower yields.

The monoethers in position 1 of D-desosamine are obtained by conventional glycosylation methods by reacting D-desosamine with the selected alcohol ($R_2OH$), in the presence of a mineral acid such as sulfuric or hydrochloric acid or an organic acid such as paratoluene sulfonic acid, optionally in an organic solvent such as N,N-dimethylformamide at a temperature of about 80° C.

The compounds in accordance with the present invention are quite particularly useful in the following fields:

(1) for the treatment of dermatologic diseases linked to a keratinization disorder based on differentiation and proliferation and principally for the treatment of acne vulgaris, comedons, polymorphs, kystic nodule acne, conglobata, senile acne, and secondary acne such as solar, medicinal and professional acne;

(2) for the treatment of other types of keratinization disorders and principally ichthyoses, ichthyosiform states, Darier malady, palmoplantaire keratodermies, leucoplasies and leucoplasiform states, lichen;

(3) for the treatment of other dermatologic diseases linked to a keratinization disorder having an inflammatory and/or immunoallergic component and, principally, all forms of psoriasis be it cutaneous, mucous or ungual, and even psoriasic rheumatism or even cutaneous atophy, such as eczema or respiratory atophy. These compounds can also be employed in certain inflammatory diseases not exhibiting a keratinization disorder;

(4) for the treatment of all dermic or epidermic proliferations be they benign or malignant, be they of viral origin such as common warts, plane warts, and verruciform epidermodysplasie. The proliferations can also be those which are induced by ultraviolet radiation, principally in the framework of baso epithelioma and cellular spino:

(5) for the treatment of other dermatologic diseases such as blistery dermatoses and collagen maladies;

(6) for the treatment of certain ophthalmologic disorders, principally corneopathies;

(7) to combat against skin aging, be it photo-induced or not; and (8) to prevent or heal the scars of epidermic and/or dermic atrophy induced by local or systemic corticosteroids, or any other form of cutaneous atrophy.

The present invention also relates to the use of the retinoic esters of D-desosamine, such as defined above, as an active agent for compositions having a therapeutic use.

The therapeutic compositions, intended principally for the treatment of the above mentioned diseases contain, in a pharmaceutically acceptable support or vehicle, at least one retinoic ester of D-desosamine or one of its salts, such as defined above by general formula (I).

These retinoic esters of D-desosamine are generally administered at a daily dosage of about 0.01 mg/kg to 50 mg/kg of body weight.

As the support for the compositions there can be used any conventional support, the active compound being found either in the dissolved state or in the dispersed state in the support or vehicle.

The administration can be effected enterally, parenterally, topically or ocularly. When administered enterally, the therapeutic compositions can be provided in the form of tablets, gelules, lozenges, syrups, suspensions, solutions, powders, granules, or emulsions. When administered parenterally, the composition can be provided in the form of solution or suspensions for perfusion or injection.

When administered topically, the therapeutic compositions, based on the retinoic esters of D-desosamine in accordance with the invention, can be provided in the form of ointments, tinctures, creams, pomades, powders, patches, impregnated pads, solutions, lotions, gels, sprays or even suspensions.

When administered ocularly, the compositions are principally eye washes.

These therapeutic compositions contain at least one retinoic ester of D-desosamine, such as defined above, in an amount ranging, preferably, from 0.001 to 5 percent by weight relative to the total weight of the composition.

The retinoic esters of D-desosamine of general formula (I) are also usefully employed in the cosmetic field and in particular for body and hair hygiene and principally for the treatment of skin having acne tendencies, for hair growth to combat falling hair, to combat against an oily appearance of the skin or hair, for protection against the harmful effects of the sun, for treatment of physiologically dry skin or as deodorants.

The present invention then also relates to cosmetic compositions containing in a cosmetically acceptable vehicle or support at least one retinoic ester of D-desosamine or one of its salts of general formula (I), this composition being provided principally in the form of a lotion, a gel, a soap, a shampoo, a stick, a spray or an aerosol foam.

The concentration of the retinoic ester of D-desosamine of formula (I) in the cosmetic compositions is generally between 0.0001 and 5 percent by weight and preferably between 0.001 and 3 percent by weight based on the total weight of said cosmetic composition.

The therapeutic and cosmetic compositions, in accordance with the present invention, can also contain inert or even pharmacodynamically or cosmetically active additives and principally: hydrating agents such as thiamorpholinone and its derivatives or urea; antiseborrheic or anti-acne agents such as S-carboxymethylcysteine, S-benzyl cysteamine and their salts and their derivatives, thioxolone or benzoyl peroxide; antibiotics such as erythromycin and its esters, neomycin, tetracyclines or 4,5-polymethylene-3-isothiazolinones; agents promoting hair growth such as "Minoxidil" (2,4-diamino-6-piperidino-pyrimidine-3-oxide) and its derivatives, Diazoxide (7-chloro-3-methyl-1,2,4-benzothiadiazine-1,1-dioxide) and Phenytoin (5,5-diphenylimidazolidine-2,4-dione); steroidal and non-steroidal anti-inflammatory agents; carotenoids and principally β-carotene; anti-psoriasic agents, such as anthralin and its derivatives and 5,8,11,14-eicosatetraynoic and 5,8,11-triynoic acids and their esters and their amides.

The compositions in accordance with the present invention, be they for therapeutic or cosmetic use, can also contain flavor improving agents, preservatives, stabilizers, humidity regulators, pH regulators, osmotic pressure modifiers, emulsifiers, UV-A and UV-B filters, antioxidants such as α-tocopherol, butylhydroxyanisole or butylhydroxytoluene.

When the compositions in accordance with the invention are intended for an anti-bacteria treatment, this treatment comprises applying a sufficient amount of the composition 2 to 3 times per day on the area of the skin to be treated and continuing this regimen for a period of time ranging from 6 to 30 weeks and preferably from 12 to 24 weeks.

The anti-bacteria compositions in accordance with the present invention can also be employed as a preventative agent, i.e. it is applied to areas of the skin susceptible of being attacked by a bacteria proliferation.

Although reference has been made more particularly to the therapeutic and cosmetic field, the retinoic esters of D-desosamine, in accordance with the present invention, can also be employed as anti-bacteria and antiseptic agents in other industrial fields such as agriculture, paper making, paints and enamels and in water treatment operations.

Comparative Studies on the Activity of Retinoic Esters of D-desosamine

The activity of retinoic esters of D-desosamines has been studied by the dilution method to determine the minimum inhibiting concentration (MIC). This method is described and employed by G. A. Denys et al, Antimicrobial Agents and Chemotherapy (1983) 23, 335–337 and J. J. Leyden et al, J.Am.Acad. Dermatol. (1983) 8 (1) 41–5, by using as the *Propionibacterium acnes* strain, strain P37 furnished by Cunliffe and Holland.

This P37 strain has been the object of studies described in the following publications:

J. Greenman, K. T. Holland and W. J. Cunliffe, Journal of General Microbiology (1983) 129, 1301–1307;

E. Ingham, K. T. Holland, G. Gowland and W. J. Cunliffe, ibid. (1980) 118, 59–65; and K. T. Holland, J. Greenman and W. J. Cunliffe, Journal of Applied Bacteriology (1979) 47, 383–384.

Selection and Isolation of Sensitive and Resistant Populations

Strain 37 is sensitive to erythromycin as evidenced by its minimum inhibiting concentration (MIC=0.78 μg/ml).

On the other hand, after 8 successive sub-cultures in the same medium (RCM* 19/20, DMSO 1/20 by volume) with the view of obtaining a progressive stabilization of this strain in this medium, a progressive resistance to erythromycin was manifested in the following form:

after spreading a standardized inoculum (DO=1.8 at 450 nm) on a gelose medium (RCM+furazolidone), in a Petri dish, a 9 mm diameter disc is deposited at its center. On the disc, 50 μg of erythromycin (in solution in DMSO) are deposited.

After 6 days at 36.C in an anaerobic medium (GAS-PAK, B.B.L. system) an inhibition zone of the growth of the strain is clearly visible (total diameter =42 mm), the majority of the colonies being situated at the periphery of the inhibition zone.

On the other hand, at the interior of the zone few colonies clearly appear.

The two types of colonies are then retained by stripping of the gelose medium (sterilized platinum loop):

(1) at the interior of the inhibition zone there are stripped off strains, called P37 E⊖ by reason of their apparent resistance to erythromycin.

(2) at 1 cm beyond the periphery of the inhibition zone, there are stripped off strains called P37 E⊕.

After isolation and culturing, the P37 E⊕ and P37 E⊖ strains effectively show very different sensitivities to erythromycin as illustrated by the following MIC values:

| MIC (μg/ml) | |
|---|---|
| P37 | 0.78 |
| P37 E⊕ | 0.78 |
| P37 E⊖ | 50 |

This phenomenon is confirmed by the study of the IC 50 (inhibiting concentration at 50% which represents the concentration of erythromycin where, at a constant culturing time, 50% survivors among the population are found

| IC (μg/ml) | |
|---|---|
| P37 | 50 |
| P37 E⊕ | 5 |
| P37 E⊖ | 100 |

The minimum concentration (MIC), expressed in μg/ml of the retinoic esters of D-desosamine tested vis-a-vis strains of *Propionibacterium acnes* P37, P37 E⊕ and P37 E⊖ and *staphilococcus epidermis* ATCC 12228, is reported in the following table:

TABLE I

| Retinoic esters of D-desosamine Compound No. (see page 5) | P37 | P37 E⊕ | P37 E⊖ | ATCC 12228 |
|---|---|---|---|---|
| 1 | 10.5 | 21 | 10.5 | 18.5 |
| 2 | 15 | 25 | 9 | 3.5 |

TABLE I-continued

| Retinoic esters of D-desosamine Compound No. (see page 5) | P37 | P37 E⊕ | P37 E⊖ | ATCC 12228 |
|---|---|---|---|---|
| 5 | 3 | 6 | 6 | 6 |
| 6 | 19 | 4.3 | 2.1 | 1.5 |
| 7 | 5.2 | 40 | 14.5 | 2.3 |
| Reference compounds | | | | |
| α,β-D-desosamine | >50 | >70 | >70 | >50 |
| O-butyl-1-α,β-D-desosamine | >100 | >100 | >110 | >100 |
| O-retinoyl (13 cis)-6-O-methyl-1-α-D-glucopyrannose | >45 | >45 | >45 | >45 |

As can be observed from the above resulting values, the retinoic esters of D-desosamine, in accordance with the present invention, exhibit excellent activity vis-a-vis *Propionibacterium acnes* and *Staphilococcus epidermis*, whereas the reference compounds are totally inactive.

Examples of Preparation

EXAMPLE 1

Preparation of O-retinoyl (13 cis)-2-O-butyl-1-α,β-D-desosamine

In a round bottom flask, under an inert atmosphere, 5 g (16.6 mmoles) of retinoic acid (13 cis) are dissolved in 35 ml of anhydrous tetrahydrofuran; the reaction mixture is cooled to 0° C. 3 ml of anhydrous pyridine and 1.6 ml (16.6 mmoles) of ethyl chloroformate are added thereto. The solution is stirred for 5 minutes and 2.5 g (30 mmoles) of sodium bicarbonate are added. Thereafter, 1.5 g (6.5 mmoles) of O-butyl-α,β-D-desosamine, previously dissolved in 150 ml of tetrahydrofuran, are added. The reaction mixture is then stirred for 10 hours while permitting the temperature thereof to rise to ambient temperature (chromatography on thin layer silica gel: methylene chloride/10% methanol). The solution is poured into 60 ml of water and then extracted with ethyl acetate. The organic phase is dried on magnesium sulfate, filtered and then concentrated under a partial vacuum. The resulting crude product is then chromatographed on a silica gel column (H.P.L.C.) by using a the eluant: ethyl acetate (5)hexane (5) thereby resulting in the isolation of 2.5 g (75% yield) of the mixture of the anomers of O-retinoyl (13 cis)-O-butyl-1-α,β-D-desosamine.

Microanalysis: $C_{32}H_{51}NO_4.2H_2O$; M=549.9

| | C | H | N |
|---|---|---|---|
| Calculated, % | 69.88 | 10.09 | 2.54 |
| Found, % | 70.25 | 9.65 | 2.45 |

Infra-red: band at 1735 cm$^{-1}$ (ester)

The NMR of $^{13}C$ (CDCl$_3$, ref. internal T.M.S.)

Negative $_\delta$ effects at 1 (−3 ppm) and at 3 (−2.8 ppm) indicate the position of the ester at 2 for the α anomer (C-1:96.5 ppm, C-3:57.50 ppm); negative $_\gamma$ effects at 1 (−2.5 ppm) and at 3(−2.3 ppm) also indicate the position of the ester at 2 for the β-anomer (C-1:102.55 ppm, C-3:63.07 ppm). The C'$_{14}$ carbon at 116.8 ppm indicates that the retinoic chain is of 13 cis configuration.

EXAMPLE 2

Preparation of O-retinoyl (all trans)-2-O-butyl-1-α,β-D-desosamine

In a round bottom flask, under an inert atmosphere, 5 g (16.6 mmoles) of retinoic acid (all trans) are dissolved in 35 ml of anhydrous tetrahydrofuran; the reaction mixture is cooled to 0° C. and then poured into 3 ml (38 mmoles) of anhydrous pyridine and 1.6 ml (16.6 mmoles) of ethyl chloroformate. The solution is stirred for 5 minutes and 2.5 g (30 mmoles) of sodium bicarbonate are added. Thereafter, 1.5 g (6.5 mmoles) of O-butyl-α,β-D-desosamine, previously dissolved in 150 ml of tetrahydrofuran, are added. The reaction mixture is then stirred for 10 hours while permitting the temperature thereof to return to ambient temperature (chromatography on thin layer silica gel: methylene chloride/10% methanol). The solution is poured into 60 ml of water and then extracted with ethyl acetate. The organic phase is dried on magnesium sulfate, filtered and then concentrated under a partial vacuum. The resulting crude product is then chromatographed on a silica gel column (H.P.L.C.) using as the eluant: ethyl acetate (5)/hexane (5) thereby resulting in the isolation of 2.7 g (81% yield) of the mixture of α,β-anomers of O-retinoyl (all trans)-2-O-butyl-1-α,β-D-desosamine.

Microanalysis: $C_{32}H_{51}NO_4.2H_2O$; M=549.9

| | C | H | N |
|---|---|---|---|
| Calculated, % | 69.88 | 10.09 | 2.54 |
| Found, % | 69.82 | 9.82 | 2.44 |

The NMR of $^{13}C$ (CDCl$_3$, ref. internal T.M.S.)

Confirmation of the stereochemistry of the all trans chain with the C'$_{14}$ carbon at 118.7 ppm without a trace of 13 cis chain.

EXAMPLE 3

Preparation of O-retinoyl (all trans)-2-O-butyl-1-α-D-desosamine

In a round bottom flask, under an inert atmosphere, 5 g (16.6 mmoles) of retinoic acid (all trans) are dissolved in 35 ml of anhydrous tetrahydrofuran; the reaction mixture is cooled to 0° C. and then poured into 3 ml (38 mmoles) of anhydrous pyridine and 1.6 ml (16.6 mmoles) of ethyl chloroformate. The solution is stirred for 5 minutes and 2.5 q (30 mmoles) of sodium bicarbonate are added. Thereafter, 1.5 g (6.5 mmoles) of O-butyl-α-D-desosamine, previously dissolved in 150 ml of tetrahydrofuran, are added. The reaction mixture is then stirred for 10 hours while permitting the temperature thereof to rise to ambient temperature (chromatography on thin layer silica gel: methylene chloride/10% methanol). The solution is poured into 60 ml of water and then extracted with ethyl acetate. The organic phase is dried on magnesium sulfate, filtered and then concentrated under a partial vacuum. The resulting crude product is then chromatographed on a silica gel column (H.P.L.C.) using as the eluant ethyl acetate (5)/hexane (5) thereby resulting in the isolation of 2.3 g (69% yield) of pure O-retinoyl (all trans)-2-O-butyl-1-α-D-desosamine.

Microanalysis: $C_{32}H_{51}NO_4.1.5H_2O$; M=540.9

|               | C     | H     | N    |
| ------------- | ----- | ----- | ---- |
| Calculated, % | 71.04 | 10.05 | 2.58 |
| Found, %      | 70.90 | 9.59  | 2.51 |

The NMR of $^{13}$C (CDCl$_3$, ref. internal T.M.S.)

Negative $\gamma$ effects at 1 ($-2.9$ ppm) and at 3 ($-2.6$ ppm) indicate the position of the ester at 2. The chemical displacement of the C'$_{14}$ (118.65 ppm) is in agreement with the all trans stereochemistry of the retinoic chain.

EXAMPLE 4

Preparation of O-retinoyl (13 cis)-2-O-butyl-1-α-D-desosamine

In a round bottom flask, under an inert atmosphere, 3 g (10 mmoles) of retinoic acid (13 cis) ar dissolved in 25 ml of anhydrous tetrahydrofuran; the reaction mixture is cooled to 0° C. and then poured into 2 ml of anhydrous pyridine and 1 ml (10 mmoles) of ethyl chloroformate. The solution is stirred for 5 minutes and 2 g of sodium bicarbonate are added. Thereafter, 1 g (4.3 mmoles) of O-butyl-α-D-desosamine, previously dissolved in 100 ml of tetrahydrofuran, are added. The reaction mixture is then stirred for 10 hours while permitting the temperature thereof to rise to ambient temperature (chromatography on thin layer silica gel: methylene chloride/10% methanol). The solution is poured into 60 ml of water and then extracted with ethyl acetate. The organic phase is dried on magnesium sulfate, filtered and then concentrated under a partial vacuum. The resulting crude product is then chromatographed on a silica gel column (H.P.L.C.) by using as the eluant: ethyl acetate (5)/hexane (5) thereby resulting in the isolation of 1.5 g (67% yield) of pure O-retinoyl (13 cis)-2-O-butyl-1-α-D-desosamine.

Microanalysis: C$_{32}$H$_{51}$NO$_4$.1.5H$_2$O; M=540.9

|               | C     | H     | N    |
| ------------- | ----- | ----- | ---- |
| Calculated, % | 71.04 | 10.05 | 2.58 |
| Found, %      | 71.05 | 9.47  | 2.52 |

Infra-red: band at 1735 cm$^{-1}$ (ester)

The NMR of $^{13}$C (CDCl$_3$, ref. intern. T.M.S.)

Negative $\gamma$ effects at 1 ($-3$ ppm) and at 3 ($-2.8$ ppm) indicate the position of the ester at 2. The C'$_{14}$ carbon (116.48 ppm) of the retinoic chain is in agreement with the 13 cis stereochemistry of the retinoic chain.

EXAMPLE 5

Preparation of O-etretinoyl (all trans)-2-O-butyl-1-α,β-D-desosamine

In a round bottom flask, under an inert atmosphere, 5 g (15.3 mmoles) of etretinoic acid (all trans) are dissolved in 35 ml of anhydrous tetrahydrofuran; the reaction mixture is cooled to 0° C. and then poured into 3 ml of anhydrous pyridine and 1.5 ml (15.3 mmoles) of ethyl chloroformate. The solution is stirred for 5 minutes and 2.5 g of sodium bicarbonate are added. Thereafter, 1.5 g (6.5 mmoles) of O-butyl-α,β-D-desosamine, previously dissolved in 150 ml of tetrahydrofuran, are added. The reaction mixture is then stirred for 10 hours while permitting the temperature thereof to rise to ambient temperature (chromatography on thin layer silica gel: methylene chloride/10% methanol). The solution is poured into 60 ml of water and then extracted with ethyl acetate. The organic phase is dried on magnesium sulfate, filtered and then concentrated under a partial vacuum. The resulting crude product is then chromatographed on a silica gel column (H.P.L.C.) by using as the eluant: ethyl acetate (5)/hexane (5) thereby resulting in the isolation of 2.7 g (78% yield) of O-etretinoyl (all trans)-2-O-butyl-1-α,β-D-desosamine.

Microanalysis: C$_{33}$H$_{49}$NO$_5$.1.5H$_2$O; M=566.9

|               | C     | H    | N    |
| ------------- | ----- | ---- | ---- |
| Calculated, % | 69.9  | 9.24 | 2.47 |
| Found, %      | 69.55 | 8.95 | 2.41 |

NMR of $^{13}$C (CDCl$_3$, ref. intern. T.M.S.)

The negative $\gamma$ effects at 1 ($-3.3$ ppm) and at 3 ($-2.6$ ppm) indicate the position of the ester at 2 for the α anomer as well as the negative $\gamma$ effects at 1 ($-2.3$ ppm) and at 3 ($-2.3$ ppm) for the β anomer.

The chemical displacement of C'$_{14}$ (119.15 ppm) is in major agreement with the all trans configuration of the chain although a trace of 13 cis chain is detected at 117.09 ppm (C'$_{14}$).

EXAMPLE 6

Preparation of O-etretinoyl (all trans)-2-O-butyl-1-α-D-desosamine

In a round bottom flask, under an inert atmosphere, 5 g (15.3 mmoles) of etretinic acid (all trans) are dissolved in 35 ml of anhydrous tetrahydrofuran; the reaction mixture is cooled to 0° C. and then poured into 3 ml of anhydrous pyridine and 1.5 ml (15.3 mmoles) of ethyl chloroformate. The solution is stirred for 5 minutes and 2.5 g of sodium bicarbonate are added. Thereafter, 1.5 g (6.5 mmoles) of O-butyl-α-D-desosamine, previously dissolved in 150 ml of tetrahydrofuran, are added. The reaction mixture is then stirred for 10 hours while permitting the temperature thereof to rise to ambient temperature (chromatography on thin layer silica gel: methylene chloride/10% methanol). The solution is poured into 60 ml of water and then extracted with ethyl acetate. The organic phase is dried on magnesium sulfate, filtered and then concentrated under a partial vacuum. The resulting crude product is then chromatographed on a silica gel column (H.P.L.C.) using as the eluant: ethyl acetate (5)/hexane (5) thereby resulting in the isolation of 2.5 g (72% yield) of pure O-etretinoyl (all trans)-2-O-butyl-1-α-D-desosamine.

Microanalysis: C$_{33}$H$_{49}$NO$_5$.0.5H$_2$O; M=548.8

|               | C     | H    | N    |
| ------------- | ----- | ---- | ---- |
| Calculated, % | 72.22 | 9.18 | 2.55 |
| Found, %      | 72.47 | 9.25 | 2.16 |

NMR of $^{13}$C (CDCl$_3$, ref. intern. T.M.S.)

The negative $\gamma$ effects at 1 ($-3.1$ ppm) and at 3 ($-2.8$ ppm) indicate the position of the ester at 2. The all trans configuration is confirmed by the chemical displacement of C'$_{14}$ at 118.75 ppm.

EXAMPLE 7

Preparation of O-etretinoyl (all trans)-2-O-butyl-1-β-D-desosamine

In a round bottom flask, under an inert atmosphere, 5 g (15.3 mmoles) of etretinic acid (all trans) are dissolved in 35 ml of anhydrous tetrahydrofuran; the reaction mixture is cooled to 0° C. and then poured into 3 ml of anhydrous pyridine and 1.5 ml (15.3 mmoles) of ethyl chloroformate. The solution is stirred for 5 minutes and 2.5 g of sodium bicarbonate are added. Thereafter, 1.5 g (6.5 mmoles) of O-butyl-$\beta$-D-desosamine, previously dissolved in 150 ml of tetrahydrofuran, are added. The reaction mixture is then stirred for 10 hours while permitting the temperature thereof to rise to ambient temperature (chromatography on thin layer silica gel: methylene chloride/10% methanol). The solution is poured into 60 ml of water and then extracted with ethyl acetate. The organic phase is dried on magnesium sulfate, filtered and then concentrated under a partial vacuum. The resulting crude product is then chromatographed on a silica gel column (H.P.L.C.) using as the eluant: ethyl acetate (5)/hexane (5) thereby resulting in the isolation of 2.1 g (60% yield) of O-etretinoyl (all trans)-2-O-butyl-1-$\beta$-D-desosamine.

Microanalysis: $C_{33}H_{49}NO_5 \cdot 1.5H_2O$; M=566.9

|  | C | H | N |
|---|---|---|---|
| Calculated, % | 69.91 | 9.24 | 2.43 |
| Found, % | 69.96 | 8.88 | 2.47 |

NMR of $^{13}C$ (CDCl$_3$, ref. intern. T.M.S.)

The negative $\gamma$ effects at 1 (−2.4 ppm) and at 3 (−2.4 ppm) indicate the position of the ester at 2. The all trans configuration of the chain is given by the chemical displacement of C'$_{14}$ at 119.06 ppm.

EXAMPLE 8

Preparation of O-retinoyl (13 cis)-2-O-decyl-2'-tetradecyl-1-$\alpha$-D-desosamine In a round bottom flask, under an inert atmosphere, 217 mg (2 mmoles) of ethyl chloroformate and 20 ml of tetrahydrofuran are introduced.

Slowly, without exceeding 0° C., a solution containing 585 mg (1.94 mmoles) of retinoic acid 13-cis, 202 mg (2 mmoles) of triethylamine and 20 ml of tetrahydrofuran is added. The reaction mixture is then stirred for 1 hour and 30 minutes at ambient temperature. The salts of triethylamine are removed by filtration.

The filtrates ar then introduced at ambient temperature and under an inert atmosphere into a round bottom flask containing 250 mg (0.48 mmoles) of O-decyl-2'-tetradecyl-1-$\alpha$-D-desosamine and 0.15 ml of anhydrous pyridine (1.3 mmoles).

The reaction mixture is then stirred for 15 hours.

The reaction is followed by chromatography on a thin layer of silica gel using as the eluant: methylene chloride (85)/methanol (5).

The reaction mixture is concentrated, then taken up in toluene and purified by chromatography on a silica gel column (H.P.L.C.) using as the eluant: ethyl acetate (6)/heptane(4) thereby resulting in the isolation of 75 mg (18% yield) of O-retinoyl (13 cis)-2-O-decyl-2'-tetradecyl-1-$\alpha$-D-desosamine accompanied by a trace of its all trans isomer.

Microanalysis:

|  | C | H | N |
|---|---|---|---|
| Calculated, % | 78.63 | 11.55 | 1.76 |
| Found, % | 78.12 | 11.45 | 1.84 |

NMR of $^{13}C$ (CDCL$_3$, ref. internal. T.M.S.)

The spectrum is in agreement with the proposed structure.

| Pharmaceutical and Cosmetic Compositions | |
|---|---|
| A - Gels for the topical treatment of acne | |
| 1. Hydoxypropyl cellulose | 1 g |
| Butylhydroxytoluene | 0.05 g |
| O-retinoyl (13 cis)-2-O-butyl-1-$\alpha$,$\beta$-D-desosamine | 0.1 g |
| Isopropanol, sufficient amount for | 100 g |
| 2. Hydroxypropyl cellulose | 1.5 g |
| Butylhydroxytoluene | 0.05 g |
| O-retinoyl (all trans)-2-O-butyl-1-$\alpha$,$\beta$-D-desosamine | 0.075 g |
| Isopropanol, sufficient amount for | 100 g |
| B - Lotion for the topical treatment of acne | |
| Butylhydroxytoluene | 0.05 g |
| O-retinoyl (13 cis)-2-O-butyl-1-$\alpha$,$\beta$-D-desosamine | 0.7 g |
| Triglycerides of $C_8$-$C_{12}$ fatty acids, sufficient amount for | 100 g |
| C - Stick for the treatment of acne | |
| White petrolatum | 52.7 g |
| Petrolatum oil | 15 ag |
| Raffinated paraffin | 32 g |
| O-retinoyl (all trans)-2-O-butyl-1-$\alpha$,$\beta$-D-desosamine | 0.3 g |

We claim:

1. A retinoic ester of D-desosamine having the formula $$R_1-\underset{\underset{O}{\|}}{C}-O \quad \text{(I)}$$

(structure showing desosamine ring with $R_1-C(=O)-O-$ at position 2, $R_2O-$ at position 1, $CH_3$ groups, and $N(CH_3)_2$)

wherein the $$R_1-\underset{\underset{O}{\|}}{C}-$$

radical is (all trans) retinoyl, (13 cis) retinoyl or etretinoyl, and

R$_2$ represents linear or branched alkyl having 1–24 carbon atoms, and the $\alpha$ and $\beta$ anomers and their mixtures and salts of said retinoic ester of formula I.

2. The retinoic ester of claim 1 wherein said linear or branched alkyl is methyl, ethyl, propyl, isopropyl, butyl, tert. butyl, octyl, nonyl, decyl, undecyl, dodecyl, tetradecyl, hexadecyl, octadecyl or 2-decyl tetradecyl.

3. The retinoic ester of claim 1 derived from etretinoic acid and having the formula

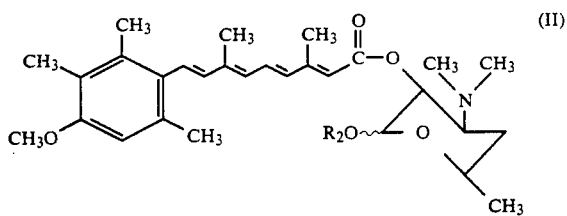

wherein

R$_2$ has the meaning given in claim 1.

4. The retinoic ester of claim 1, derived from (all trans) or (13 cis) retinoic acid and having the formula

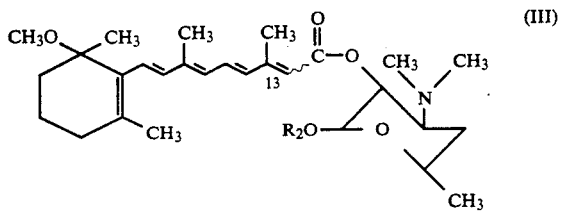

wherein

R$_2$ has the meaning given in claim 1.

5. The retinoic ester of claim 1 selected from the group consisting of

O-retinoyl (13 cis)-2-O-butyl-1-α,β-D-desosamine,
O-retinoyl (all trans)-2O-butyl-1-α,β-D-desosamine,
O-retinoyl (all trans)-2-O-butyl-1-α-D-desosamine,
O-retinoyl (13 cis)-2-O-butyl-1-α-D-desosamine,
O-etretinoyl (all trans)-2-O-butyl-1-α,β-D-desosamine,
O-etretinoyl (all trans)-2-O-butyl-1-α-D-desosamine,
O-etretinoyl (all trans)-2-O-butyl-1-β-D-desosamine,
O-retinoyl (13 cis)-2-O-methyl-1-α,β-D-desosamine,
O-retinoyl (all trans)-2-O-decyl-2′-tetradecyl-1-α,β-D-desosamine, and
O-retinoyl (13 cis)-2-O-decyl-2′-tetradecyl-1-α,β-D-desosamine.

6. A process for the preparation of the retinoic ester of claim 1 comprising reacting an excess of a mixed anhydride of etretinic acid or (all trans) or (13 cis) retinoic acid, prepared in situ, with a monoether in position 1 of D-desosamine, in an organic solvent medium.

7. The process cf claim 6 wherein said organic solvent is tetrahydrofuran, alone or in admixture with pyridine or N,N-dimethylformamide.

8. A pharmaceutical composition comprising in a pharmaceutically acceptable vehicle suitable for enteral, parenteral, topical or ocular administration, at least one retinoic ester of claim 1.

9. The pharmaceutical composition of claim 8 wherein said vehicle is suitable of topical administration and said retinoic ester is present in an amount ranging from 0.001 to about 5 percent by weight based on the total weight of said composition.

10. A process for treating a dermatologic, rheumatismal, respiratory or ophthalmologic disease or disorder comprising administering to a person suffering from said disease or disorder an effective amount of the pharmaceutical composition of claim 8.

11. A cosmetic composition comprising in a cosmetically acceptable vehicle at least one retinoic ester of claim 1.

12. The cosmetic composition of claim 11 wherein said retinoic ester is present in an amount ranging from 0.0001 to 5 percent by weight based on the total weight of said composition.

13. The cosmetic composition of claim 11 wherein said retinoic ester is present in an amount ranging from 0.001 to 3 percent by weight based on the total weight of said composition.

14. A process for combatting skin aging comprising applying to the skin an effective amount of the composition of claim 12.

15. A process for combatting bacteria proliferation on the skin comprising applying to the area of the skin to be treated an effective amount of the composition of claim 12.

* * * * *